(12) United States Patent
Wessels et al.

(10) Patent No.: US 9,687,277 B2
(45) Date of Patent: Jun. 27, 2017

(54) IMPLANTATION SYSTEM FOR TREATMENT OF A DEFECTIVE CURVATURE OF THE SPINAL COLUMN

(75) Inventors: Martijn Wessels, Utrecht (NL); Edsko Evert Geert Hekman, Utrecht (NL); Gijsbertus Jacobus Verkerke, Utrecht (NL)

(73) Assignees: Stichting voor de Technische Wetenschappen, Utrecht (NL); Universiteit Twente, Enschede (NL)

( * ) Notice: Subject to any disclaimer, the term of this patent is extended or adjusted under 35 U.S.C. 154(b) by 94 days.

(21) Appl. No.: 14/401,374

(22) PCT Filed: May 16, 2012

(86) PCT No.: PCT/NL2012/050340
§ 371 (c)(1),
(2), (4) Date: Mar. 27, 2015

(87) PCT Pub. No.: WO2013/172700
PCT Pub. Date: Nov. 21, 2013

(65) Prior Publication Data
US 2015/0342646 A1    Dec. 3, 2015

(51) Int. Cl.
*A61B 17/70* (2006.01)

(52) U.S. Cl.
CPC ...... *A61B 17/7002* (2013.01); *A61B 17/7004* (2013.01); *A61B 17/7011* (2013.01);
(Continued)

(58) Field of Classification Search
CPC ..................... A61B 17/70–17/7056
See application file for complete search history.

(56) References Cited

U.S. PATENT DOCUMENTS 5,366,455 A * 11/1994 Dove ................. A61B 17/7053
606/250
5,437,669 A * 8/1995 Yuan ................. A61B 17/7047
606/264

(Continued)

FOREIGN PATENT DOCUMENTS

EP      0470660 A1    2/1992
FR      2872021 A1    12/2005
(Continued)

*Primary Examiner* — Eduardo C Robert
*Assistant Examiner* — Steven Cotroneo
(74) *Attorney, Agent, or Firm* — Schwegman Lundberg & Woessner, P.A.

(57) ABSTRACT

An implantation system for treatment of a defective curvature of the spinal column comprises an elongated element, a first bone fixation element being fixedly attached to said elongated element, a second bone fixation element, and guiding structure through which the second bone fixation element is slidably and contactingly connected to the elongated element. The elongated element has bending resilience and/or torsional resilience for applying corrective force action to the spinal column. A special arrangement of the guiding structure provides automatical adjustment of the corrective force action in dependence of growth of the spinal column. The system allows for good flexibility of the spine and for a natural healthy growth of the spine, while it avoids re-operations and implant adjustments.

15 Claims, 8 Drawing Sheets

(52) U.S. Cl.
CPC ...... *A61B 17/7028* (2013.01); *A61B 17/7031* (2013.01); *A61B 17/7041* (2013.01); *A61B 17/7053* (2013.01); *A61B 17/7001* (2013.01); *A61B 17/7049* (2013.01)

(56) References Cited

U.S. PATENT DOCUMENTS

| | | | | |
|---|---|---|---|---|
| 5,672,175 | A * | 9/1997 | Martin | A61B 17/025 606/105 |
| 5,733,284 | A * | 3/1998 | Martin | A61B 17/025 606/248 |
| 7,867,256 | B2 * | 1/2011 | Schlaepfer | A61B 17/7031 606/257 |
| 2001/0037111 | A1 * | 11/2001 | Dixon | A61B 17/66 606/261 |
| 2003/0109880 | A1 * | 6/2003 | Shirado | A61B 17/7028 606/328 |
| 2003/0220643 | A1 * | 11/2003 | Ferree | A61B 17/7023 623/17.16 |
| 2004/0116931 | A1 * | 6/2004 | Carlson | A61B 17/7044 606/70 |
| 2006/0282073 | A1 * | 12/2006 | Simanovsky | A61B 17/707 606/282 |
| 2007/0093815 | A1 * | 4/2007 | Callahan | A61B 17/7026 606/279 |
| 2010/0036425 | A1 * | 2/2010 | Barrus | A61B 17/7032 606/264 |

FOREIGN PATENT DOCUMENTS

| | | |
|---|---|---|
| WO | WO-0217803 A2 | 3/2002 |
| WO | WO-2010030906 A1 | 3/2010 |

* cited by examiner

Fig. 8

IMPLANTATION SYSTEM FOR TREATMENT OF A DEFECTIVE CURVATURE OF THE SPINAL COLUMN

PRIORITY APPLICATIONS

This application is a U.S. National Stage Filing under 35 U.S.C. 371 from International Application No. PCT/NL2012/050340, filed on 16 May 2012, and published as WO 2013/172700 A1 on 21 Nov. 2013; which application and publication are incorporated herein by reference in their entirety.

The invention relates to an implantation system for treatment of a defective curvature of the spinal column.

Such a disorder of the spinal column is often referred to as "scoliosis". A commonly used treatment of scoliosis is to perform an operation, wherein an implant is fixedly attached to at least the defective longitudinal part of the spine, mostly at the posterior side of the spine. Therein, the implant has at least one rod, having high bending and torsional stiffness. The shape of that rod closely resembles the desired (i.e. "healthy") curvature of the defective part of the spine. The rod is provided with at least two anchoring elements, which are fixedly attached to the rod at distant locations in longitudinal direction of the rod. During the performing of the operation the defective part of the spine is instantaneously deformed as much as possible so as to match its desired curvature as much as possible. With the spine being in this corrected state, one of the two anchoring elements is fixedly attached to one vertebra of the defective spine, while the other anchoring element is fixedly attached to another vertebra of the defective spine. Thus, the implanted rod, having high stiffness, secures the corrected state of the spine.

This commonly used treatment goes hand in hand with the occurrence of fusion of adjacent vertebrae of the treated part of the spine. This fusion gradually occurs after the operation due to mutual immobility of said adjacent vertebrae, which is a consequence of the implanted high-stiffness rod that secures the treated part of the spine. For this commonly used treatment, surgeons consider such fusion as a desirable effect, since it stabilizes the imposed, corrected curvature of the spine. In addition, such fusion lightens the implant's task and thereby prevents eventual failure of the implant, which usually is unable to long-lastingly withstand heavy loads. For these reasons, in performing this commonly used treatment, surgeons in fact usually apply additional measures aiming at further stimulating fusion and the speed thereof, such as the additional measure of roughening vertebrae surfaces.

However, this commonly used treatment has several drawbacks. One of the drawbacks is that the implanted device and/or the fused vertebrae impair the patient's possibilities to perform various flexible movements of the spine. Further drawbacks for example relate to problems associated with growing spinal columns of children. In fact, the abovementioned implanted devices impair a natural healthy growth of the spine. For example, an implant being posteriorly fixed to a spine may lead to a spine that undesirably grows in a backwards bending fashion. Hence, in view of such growth-related drawbacks, this commonly used treatment requires re-operations to be carried out, which is very undesirable for many evident reasons.

In view of the abovedescribed drawbacks, WO02/17803A2 and WO2010/030906A1 disclose alternative implants aiming at addressing such drawbacks related to reduced flexibility of the spine and related to growth of the spinal column. Such an alternative known implant not only has at least one vertebra-anchoring element, which is fixedly attached to a rod, but also at least one other vertebra-anchoring element, which is slidably connected to the same rod. Thanks to the slidability of the rod relative to the other vertebra-anchoring element, such an alternative implanted configuration, as compared to the abovedescribed commonly used implanted configurations, provides improved flexibility of the spine and reduces some of the abovementioned growth-related drawbacks. Amongst others, such an alternative implanted configuration, as compared to the abovedescribed commonly used implanted configurations, aims at avoiding fusion of vertebrae, instead of aiming at stimulating such fusion.

However, the alternative implants known from WO02/17803A2 and WO2010/030906A1 still have drawbacks, which are explained as follows.

In case the rod of such an alternative known implanted device has relatively high stiffness, it is disadvantageous that the flexibility of the spine still is poor, while fusion of vertebrae is not effectively prevented then.

If, on the other hand, the rod of such an alternative known implanted device would have relatively low stiffness, it is disadvantageous that the corrective force action that the rod applies to the spinal column for correcting the defective curvature of the spinal column, decreases with progressing growth of the spine. The reason for this decreasing corrective force action is that the corrective deformation of the spinal column achieved by a low-stiffness-rod (which of course is much lower than the instantaneous large corrective deformation achieved by a high-stiffness-rod) only gradually and slowly increases in the course of time when the patient is wearing the implant over the years. By such a gradual increase of the corrective deformation of the spinal column, the rod gradually becomes less tensioned and, accordingly, the corrective force action that the rod applies to the spinal column gradually decreases. In addition, as the spine grows during the years, the distance between the two abovementioned vertebra-anchoring elements (one of which is slidable relative to the rod), increases which has a further reducing influence on the corrective force action that the rod applies to the spinal column. And, on top of that, contrary to the fact that the corrective force action in fact is gradually decreasing over time, the higher loads that the patient's spine has to carry due to the patient's growing body and weight in fact require a gradual increase of the corrective force action delivered by the rod. Hence, the application of a low-stiffness-rod in such an alternative known implanted device with partly slidable rod still requires re-operations/adjustments to be carried out, which is very undesirable.

In light of the above, it is an object of the invention to provide at least an alternative solution according to which a defective curvature of the spinal column is treated, while maintaining as much as possible:

flexibility of the spine; and/or
a natural healthy growth of the spine; and/or
efficiency and effectivity of the corrective treatment over time, while avoiding re-operations and implant adjustments as much as possible.

For that purpose, the invention provides an implantation system for treatment of a defective curvature of the spinal column of a patient, the system comprising:

at least one element being elongated in a longitudinal direction;
at least one first bone fixation element being arranged for being fixedly attached to a first vertebra of said spinal column, the first bone fixation element being fixedly attached to said elongated element at a first location along said longitudinal direction of the elongated element;

at least one second bone fixation element being arranged for being fixedly attached to a second vertebra of said spinal column, said second vertebra being different from said first vertebra; and guiding structure through which the second bone fixation element is slidably and contactingly connected to the elongated element for guiding the second bone fixation element relative to the elongated element in a sliding range along said longitudinal direction, said sliding range being distant from said first location;

wherein the elongated element has bending resilience and/or torsional resilience for resiliently applying in mounted condition of the implantation system, via said first and second bone fixation elements and via said first and second vertebrae, corrective bending and/or torsional force action to said spinal column for correcting said defective curvature;

wherein in at least part of said sliding range the transverse cross-sectional shape of said elongated element is different from that of a single rod having a circular transverse cross-sectional circumference; and wherein said guiding structure is arranged in such manner that, in said mounted condition and under application of said corrective force action, in response to longitudinal growth of said spinal column, the responsive sliding of said second bone fixation element relative to said elongated element in said at least part of said sliding range away from the first location causes said corrective force action to be higher than if in said at least part of said sliding range the transverse cross-sectional shape of the elongated element would have been the same as that of said single rod having a circular transverse cross-sectional circumference.

Hence, the implantation system according to the invention not only has said first bone fixation element, which is fixedly attached to the elongated element, but also the second bone fixation element, which is slidably connected to that elongated element. In this respect, the implantation system according to the invention is similar to the abovedescribed implants known from WO02/17803A2 and WO2010/030906A1. Therefore, already for similar reasons as for these known implants, the implantation system according to the invention provides improved flexibility of the spine and reduces some of the growth-related drawbacks. Amongst others, the implantation system according to the invention aims at avoiding fusion of vertebrae.

In fact, these specific improvements may be better than for these known implants, since the implantation system according to the invention allows for resiliently applying in its mounted condition relatively low bending resilience and/or torsional resilience of the elongated element, which relatively low resiliences further improve the flexibility of the spine and further prevent fusion of vertebrae. The reasons that low resiliences may be applied in a system according to the invention, lie in the recited transverse cross-sectional shape of said elongated element in combination with the recited guiding structure. That is, for a system according to the invention in response to longitudinal growth of said spinal column, the responsive sliding of said second bone fixation element relative to said elongated element in said at least part of said sliding range away from the first location causes said corrective force action to be higher than possible for the abovedescribed implants known from WO02/17803A2 and WO2010/030906A1. Note that for the lastmentioned known implants the elongated element is a single rod having a circular transverse cross-sectional circumference and that such circularity together with the different guiding structure of these known implants unavoidably brings along loss of corrective force action during such sliding, as explained. Hence, as compared with and contrary to the implants known from WO02/17803A2 and WO2010/030906A1, by using low resiliences of the elongated element the implantation system according to the invention provides further improved flexibility of the spine, while at the same time preserving efficiency and effectivity of the corrective treatment over time, i.e. when the spinal column grows, thus avoiding undesirable re-operations and implant adjustments as much as possible.

It is remarked that according to the invention said loss of corrective force action during such sliding is counteracted not only when applying relatively low bending resilience and/or torsional resilience of the elongated element, but also when applying relatively high bending resilience and/or torsional resilience of the elongated element.

In summary, for a system according to the invention, the transverse cross-sectional shape of the elongated element in combination with the special arrangement of the guiding structure provides automatical adjustment of the corrective force action in dependence of growth of the spinal column. The system according to the invention allows for good flexibility of the spine and for a natural healthy growth of the spine, while it avoids re-operations and implant adjustments.

In a preferable embodiment of the invention said guiding structure is realized in that the elongated element is shaped to comprise a resilient U-shaped portion, said U-shaped portion having two legs and an interconnecting part interconnecting said two legs, wherein said U-shaped portion with its interconnecting part is facing away from said first location, wherein one of said two legs is a free ending leg of the elongated element, said free ending leg having bending resilience, wherein said sliding range is extending along at least part of said U-shaped portion, and wherein said sliding and contacting connection is present between the second bone fixation element and at least said free ending leg of the U-shaped portion.

Thanks to said U-shaped portion, loss of corrective bending and/or torsional force action is counteracted over time, i.e. when the spinal column grows. That is, such loss of corrective force action can be reduced, said corrective force action can be maintained or said corrective force action can even be increased when the spinal column grows. Such a U-shaped portion not only provides reliability of the system, but also is easy to manufacture.

In relation to such a U-shaped portion, it is remarked that the invention may, more in general, be embodied in an implantation system for treatment of a defective curvature of the spinal column of a patient, the system comprising:

at least one element being elongated in a longitudinal direction;

at least one first bone fixation element being arranged for being fixedly attached to a first vertebra of said spinal column, the first bone fixation element being fixedly attached to said elongated element at a first location along said longitudinal direction of the elongated element;

at least one second bone fixation element being arranged for being fixedly attached to a second vertebra of said spinal column, said second vertebra being different from said first vertebra; and guiding structure through which the second bone fixation element is slidably and contactingly connected to the elongated element for guiding the second bone fixation element relative to the elongated element in a sliding range along said longitudinal direction, said sliding range being distant from said first location;

wherein the elongated element has bending resilience and/or torsional resilience for resiliently applying in mounted condition of the implantation system, via said first and second bone fixation elements and via said first and second vertebrae, corrective bending and/or torsional force action to said spinal column for correcting said defective curvature;

characterized in that said guiding structure is realized in that the elongated element is shaped to comprise a resilient U-shaped portion, said U-shaped portion having two legs and an interconnecting part interconnecting said two legs, wherein said U-shaped portion with its interconnecting part is facing away from said first location, wherein one of said two legs is a free ending leg of the elongated element, said free ending leg having bending resilience, wherein said sliding range is extending along at least part of said U-shaped portion, and wherein said sliding and contacting connection is present between the second bone fixation element and at least said free ending leg of the U-shaped portion.

In another preferable embodiment of the invention said guiding structure comprises helically shaped structure defining a helical path for said guiding the second bone fixation element relative to the elongated element in the sliding range.

Thanks to said helically shaped structure, loss of corrective torsional force action is counteracted over time, i.e. when the spinal column grows. That is, such loss of corrective force action can be reduced, said corrective force action can be maintained or said corrective force action can even be increased when the spinal column grows. Such a helically shaped structure not only provides reliability of the system, but also is easy to manufacture.

In relation to such a helically shaped structure, it is remarked that the invention may, more in general, be embodied in an implantation system for treatment of a defective curvature of the spinal column of a patient, the system comprising:

at least one element being elongated in a longitudinal direction;

at least one first bone fixation element being arranged for being fixedly attached to a first vertebra of said spinal column, the first bone fixation element being fixedly attached to said elongated element at a first location along said longitudinal direction of the elongated element;

at least one second bone fixation element being arranged for being fixedly attached to a second vertebra of said spinal column, said second vertebra being different from said first vertebra; and guiding structure through which the second bone fixation element is slidably and contactingly connected to the elongated element for guiding the second bone fixation element relative to the elongated element in a sliding range along said longitudinal direction, said sliding range being distant from said first location;

wherein the elongated element has bending resilience and/or torsional resilience for resiliently applying in mounted condition of the implantation system, via said first and second bone fixation elements and via said first and second vertebrae, corrective bending and/or torsional force action to said spinal column for correcting said defective curvature;

characterized in that said guiding structure comprises helically shaped structure defining a helical path for said guiding the second bone fixation element relative to the elongated element in the sliding range.

In principle, there are various ways of realizing such a helically shaped structure, for example by applying helical grooves and/or helical ribs to a portion of the elongated element in the sliding range and/or to a portion of the second bone fixation element.

In a further preferable embodiment of the invention said helically shaped structure is realized in that the elongated element is shaped to comprise a helically shaped portion, wherein said sliding range is extending along at least part of said helically shaped portion, and wherein said sliding and contacting connection is present between the second bone fixation element and said helically shaped portion in such manner that, when the second bone fixation element slides along said helically shaped portion in said longitudinal direction, the orientation of the second bone fixation element relative to said helically shaped element follows said helical path.

In all embodiments of an implantation system according to the invention, the implantation system may comprise at least two specimens of said at least one second bone fixation element, each of said two specimens being associated with the same elongated element, wherein said two specimens are mutually lying on opposite sides of said first location, one of said two specimens being associated with a first corresponding one of said second vertebra and with a first corresponding one of said sliding range, the other one of said two specimens being associated with a second corresponding one of said second vertebra and with a second corresponding one of said sliding range.

In all embodiments of an implantation system according to the invention, the implantation system may comprise a plurality of said at least one elongated element, each one of said plurality being associated with the same first bone fixation element and with the same second bone fixation element.

In all embodiments of an implantation system according to the invention, at least one of said first bone fixation element may comprise two first bone fixators, being mutually spaced in a direction transverse to said longitudinal direction, and a first bridging part, which fixedly attaches the two first bone fixators relative to one another, and which bridging part is fixedly attached to the elongated element at said first location, each of said two first bone fixators being arranged for being fixedly attached to one and the same vertebra.

In all embodiments of an implantation system according to the invention, at least one of said second bone fixation element may comprise two second bone fixators, being mutually spaced in a direction transverse to said longitudinal direction, and a second bridging part, which fixedly attaches the two second bone fixators relative to one another, wherein said sliding and contacting connection is present between said second bridging part and the elongated element, each of said two second bone fixators being arranged for being fixedly attached to one and the same vertebra.

These and other aspects of the invention will be apparent from and elucidated with reference to the embodiments described hereinafter by way of non-limiting examples only and with reference to the schematic figures in the enclosed drawing.

Figure 1:
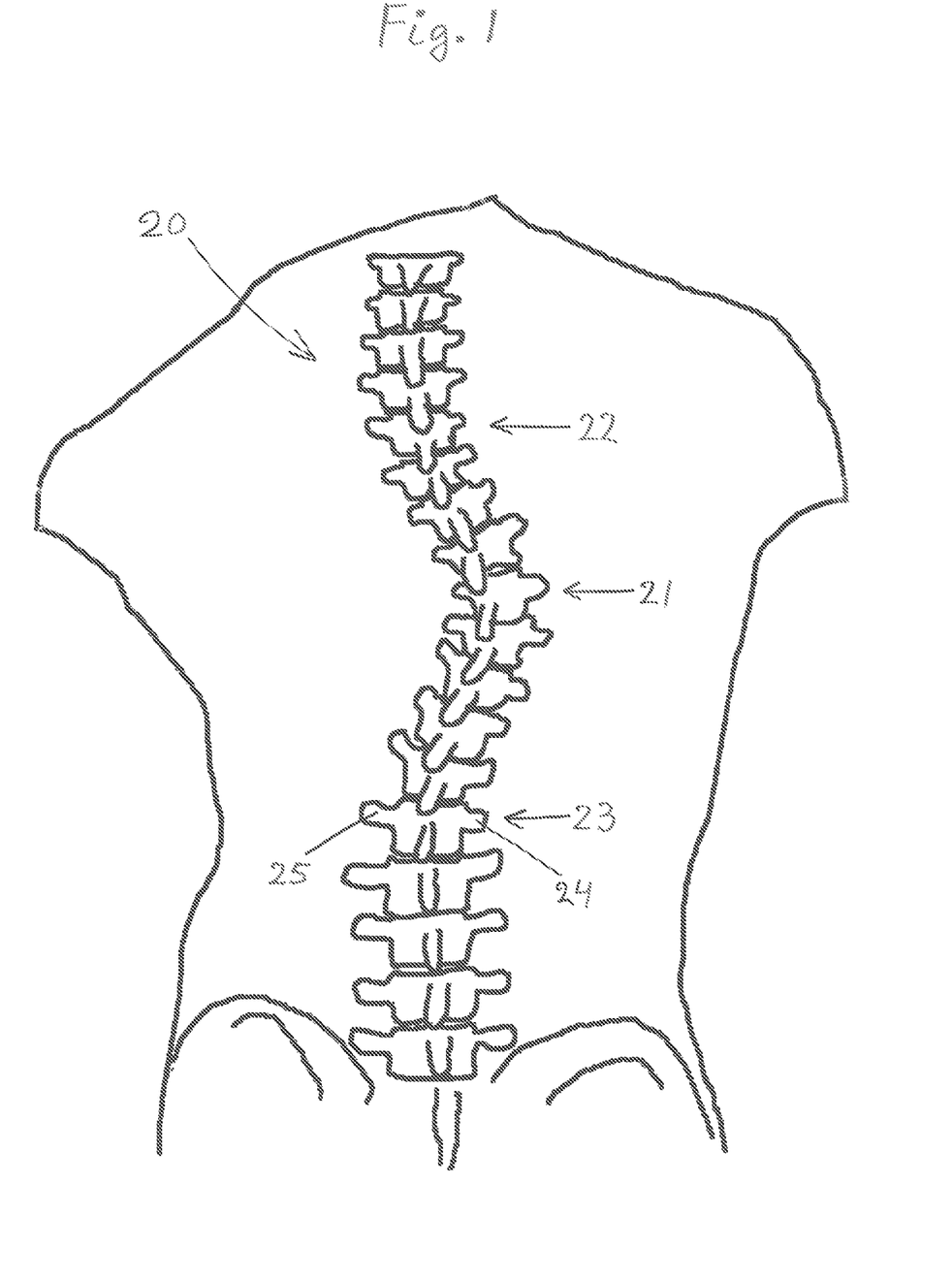
FIG. 1 shows, in rear view, an example of a defective curvature of the spinal column of a patient.

FIG. 1 shows a spinal column 20, hereinafter also referred to as spine 20, having a number of vertebrae, of which three vertebrae have been identified with reference numerals, i.e. a first vertebra 21, a second vertebra 22 and another second vertebra 23. The spine 20 has a defective curvature ("scoliosis"), which is substantially extending between the two vertebrae 22 and 23. The vertebra 21 is substantially located at the "apex" of the defective curvature. The laterally protruding bone parts of the vertebrae are called "transverse processes". FIG. 1 shows the transverse processes 24 and 25 of vertebra 23.

In the rear view of FIG. 1 the defective curvature of spine 20 is clearly visible as a substantial lateral defective deformation of the spine. However, it should be understood that in most cases of scoliosis lateral defective deformation goes hand in hand with substantial torsional defective deformation relative to the longitudinal direction of the spine. Since FIG. 1 is a rear view, such torsional deformation, although present in spine 20, is less clearly visible in FIG. 1.

Figure 2:
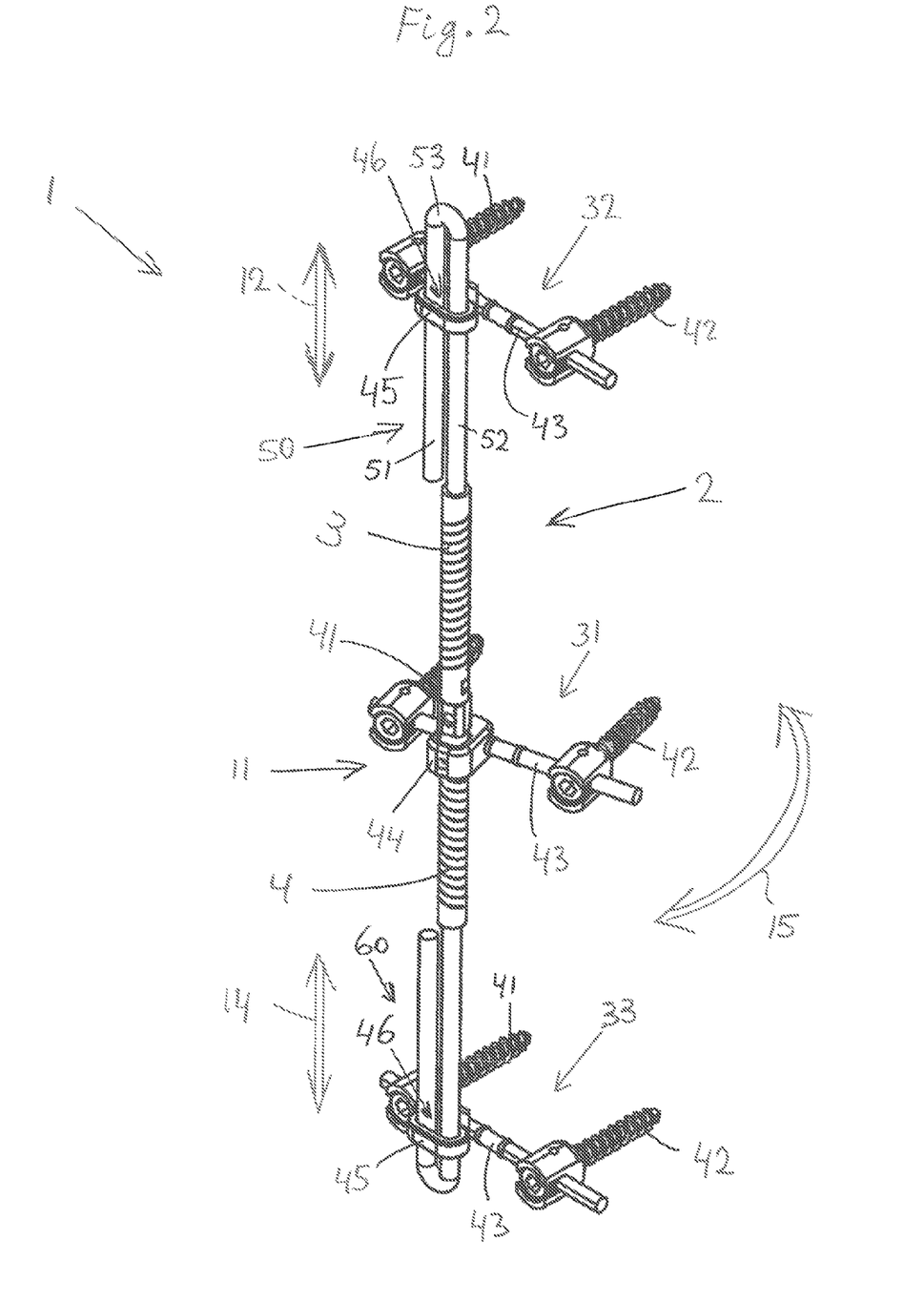
FIG. 2 shows, in a perspective view, an example of an embodiment of an implantation system according to the invention.

Reference is now made to FIG. 2, which shows the system 1 as an example of an embodiment of an implantation system according to the invention. System 1 comprises an elongated element 2, a first bone fixation element 31, a second bone fixation element 32 and another second bone fixation element 33.

Each of these bone fixation elements 31, 32 and 33 is arranged for being fixedly attached to a vertebra of a spinal column. For example, element 31 may be fixedly attached to vertebra 21 of spine 20, element 32 may be fixedly attached to vertebra 22 of spine 20 and element 33 may be fixedly attached to vertebra 23 of spine 20. For that purpose, each of these elements 31, 32 and 33 comprises two bone fixators 41 and 42, being mutually spaced in a direction transverse to the longitudinal direction of element 2, and a bridging part 43, which fixedly attaches the two bone fixators 41 and 42 relative to one another.

The bridging part 43 of first bone fixation element 31 is fixedly attached to the elongated element 2 at first location 11 along the longitudinal direction of element 2. In the shown example, this is realized by means of the shown attachment element 44.

On one side of the first location 11 the element 2 comprises a first helical spring 3, while on the other side of the first location 11 the element 2 comprises a second helical spring 4. In the shown example, the helical pitch of the first helical spring 3 has an opposite direction relative to the helical pitch of the second helical spring 4. The springs 3 and 4 provide the element 2 at least with torsional resilience. It is remarked that the springs may also be designed so as to provide, by themselves, the element 2 with additional bending resilience in whatever degree.

In the example of FIG. 2, the element 2 comprises a first U-shaped portion 50 on a side of the first helical spring 3 facing away from the first location 11, while the element 2 comprises a second U-shaped portion 60 on a side of the second helical spring 4 facing away from the first location 11. The second bone fixation element 32 comprises a connection element 45 which is fixedly attached to the bridging part 43 of element 32. The connection element 45 comprises a passageway 46 through which the legs of the U-shaped portion 50 are extending. Via this connection element 45, the second bone fixation element 32 is slidably and contactingly connected to the elongated element 2 for guiding the second bone fixation element relative to the elongated element in sliding range 12 along the longitudinal direction of element 2.

Similarly, the other second bone fixation element 33 comprises a similar connection element 45 which is fixedly attached to the bridging part 43 of element 33. Here, it are the legs of the U-shaped portion 60 which are extending through the passageway 46 of this similar connection element 45. This way, also the other second bone fixation element 33 is slidably and contactingly connected to the elongated element 2, this time for guiding the other second bone fixation element 33 relative to the elongated element in sliding range 14 along the longitudinal direction of element 2.

For each of the bone fixation elements 31, 32 and 33, both bone fixators 41 and 42 are arranged for being fixedly attached to one and the same vertebra. In the shown example, the bone fixators 41 and 42 are pedicle screws, various kinds of which are known in the art. However, instead of pedicle screws, various other kinds of bone fixators are possible, such as, for example, lamina hooks and sublaminar wires. Since, as explained in the introduction above, the implantation system according to the invention aims at avoiding fusion of vertebrae, it is preferable to use bone fixators which avoid damaging the vertebrae and especially the joints between the vertebrae. Hence, in a preferable embodiment, the bone fixators may be in the form of straps 441 and 442 shown in the embodiment of FIG. 8, which shows a second bone fixation element 432 comprising the same bridging part 43 and the same connection element 45 as those of the second bone fixation element 32 of FIG. 2. Such straps 441 and 442 may be fitted around the transverse processes 24 and 25 of a vertebra (see FIG. 1) and prevent damage to the vertebrae.

Figure 7:
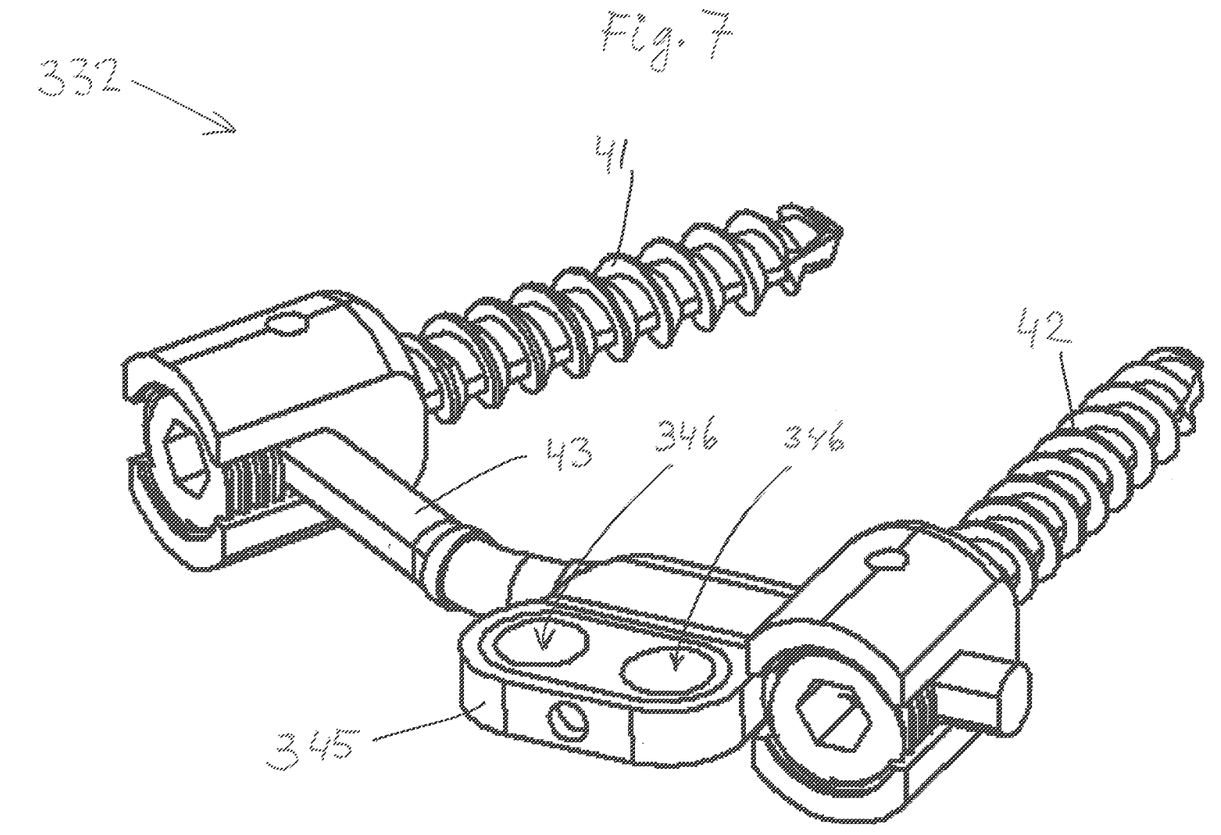
FIG. 7 shows, in a perspective view, an example of an embodiment of a second bone fixation element of an implantation system according to the invention.
Figure 8:
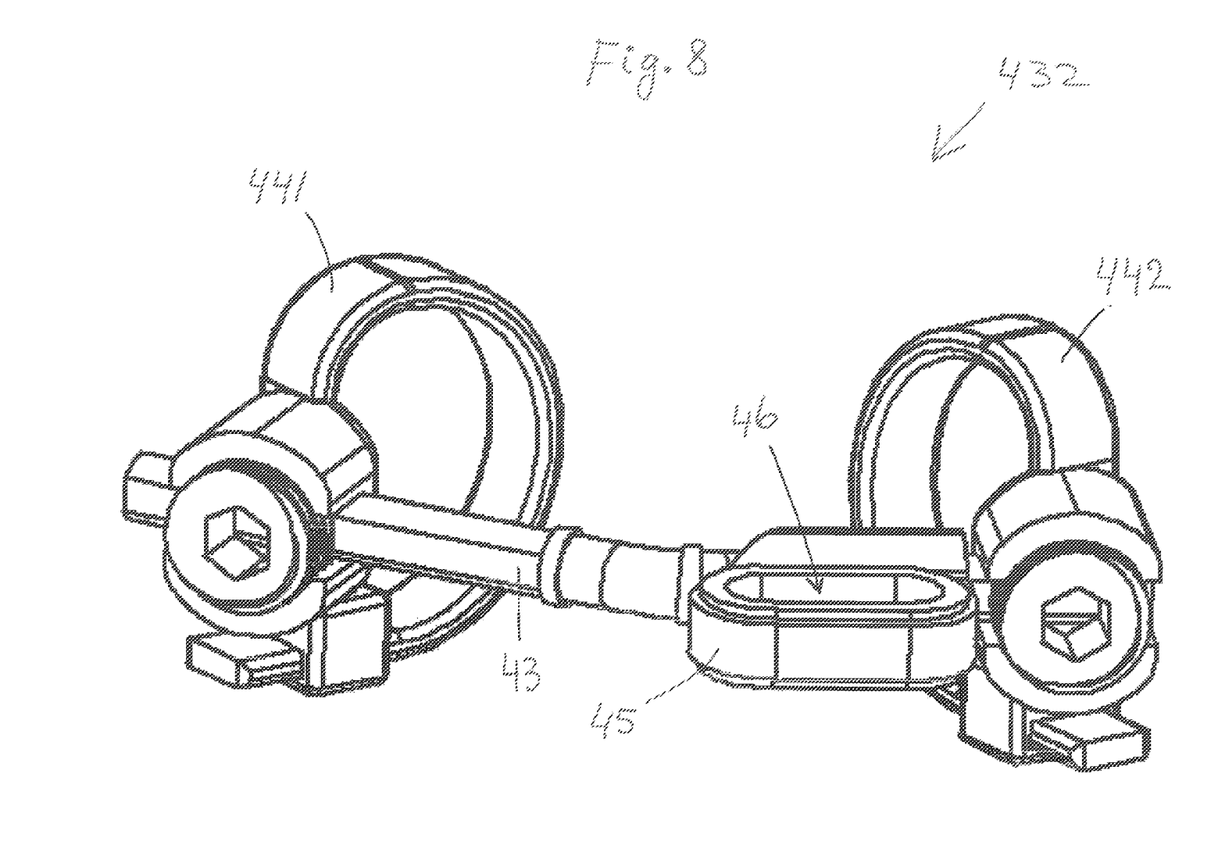
FIG. 8 shows, in a perspective view, an example of another embodiment of a second bone fixation element of an implantation system according to the invention.

It is noted, by the way, that FIG. 8 more clearly shows the connection element 45 of the second bone fixation element 32 and of the other second bone fixation element 33 of FIG. 2. Particularly, FIG. 8 more clearly shows the abovementioned passageway 46 through the connection element 45. From FIG. 8 it can be seen that the passageway 46 has a slot-like transverse cross-sectional shape. This slot-like shape allows the two legs of the U-shaped portion 50, or 60, both of which are extending through the passageway 46, to laterally move towards and away from one another when one or both of these legs are resiliently deforming. However, in some cases, it is not strictly necessary or desired to allow the two legs of such a U-shaped portion to thus move towards and away from one another. In such cases a connection element can be used that comprises two separate passageways, such as the connection element 345 of the second bone fixation element 332 shown in FIG. 7. In FIG. 7 it can be seen that the connection element 345 has two separate passageways 346, in each of which one such leg of such a U-shaped portion may be received. Note that, purely by way of example, the second bone fixation element 332 shown in FIG. 7, is provided with pedicle screws 41 and 42.

Reference is now made to FIG. 2 again. A mounted condition of the implantation system 1 may for example be obtained when the bone fixators 41 and 42 of the first bone fixation element 31 are fixedly attached to vertebra 21 of FIG. 1, and the bone fixators 41 and 42 of the second bone fixation element 32 are fixedly attached to vertebra 22 of FIG. 1, and the bone fixators 41 and 42 of the other second bone fixation element 33 are fixedly attached to vertebra 23 of FIG. 1. The system 1 can be brought in its mounted condition in such manner that, by means of suitable pretensioning of the helical springs 3 and 4, these helical springs 3 and 4 in the mounted condition are resiliently applying, via the elements 31, 32 and 33 and via the vertebrae 21, 22 and 23, corrective torsional force action to the spine 20 for correcting the defective torsional curvature of the spine 20. Double arrow 15 in FIG. 2 illustrates possible relative rotational movements, around the longitudinal direction of element 2, of the first bone fixation element 31 relative to the second bone fixation element 32, as well as of the first bone fixation element 31 relative to the other second bone fixation element 33. These relative rotational movements are possible in said mounted condition, as allowed by and under influence of the resiliency of the helical springs 3 and 4.

Figures 4A, 4B:
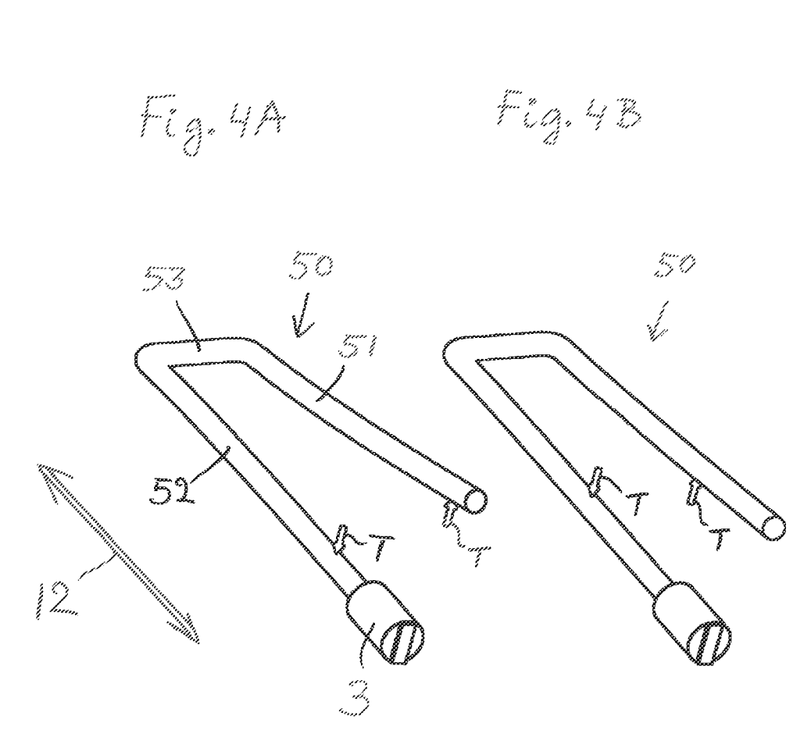
FIGS. 4A, 4B and 4C respectively show, in mutually identical perspective views, three different tensioned deformation states of an example of an embodiment of part of an elongated element of an implantation system according to the invention, said part extending at least in a sliding range as defined by the recited invention.
Figure 4C:
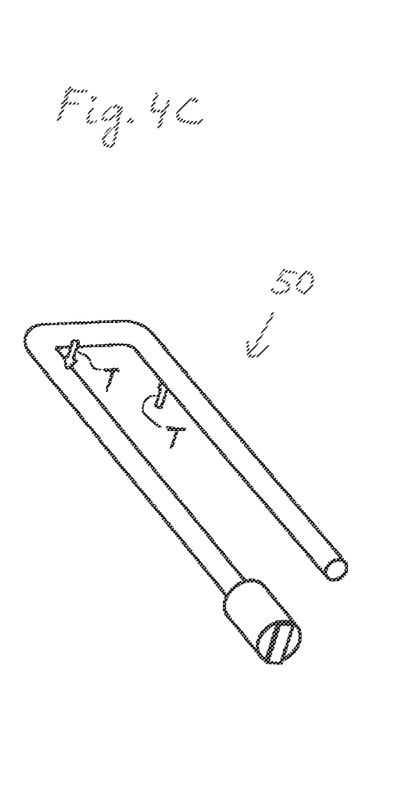

Now, with additional reference to FIGS. 4A, 4B and 4C, it is elucidated what happens when the spine 20 is growing in the course of time, which is the case when the system 1 is implanted into a growing child. The lastmentioned figures show the U-shaped portion 50 of FIG. 2. U-shaped portion 50 has two legs, 51 and 52, and an interconnecting part 53 interconnecting said two legs, wherein said U-shaped portion 50 with its interconnecting part 53 is facing away from the first location 11. One of said two legs is a free ending leg 51 of the elongated element 2, said free ending leg having bending resilience. The other leg 52 is connected to the helical spring 3. The sliding range 12 is extending along at least part of U-shaped portion 50. During longitudinal growth of the spine 20, vertebra 22 moves farther away from vertebra 21. This means that, averagely speaking, the connection element 45 will move farther away from the first location 11 in the course of time, i.e. in the direction of interconnecting part 53 of U-shaped portion 50. This means that the torque being delivered by helical spring 3 and, via the U-shaped portion 50, being transmitted to the connection element 45, which torque is indicated by the arrows T in FIGS. 4A, 4B and 4C, will, averagely speaking, be transmitted at locations in the sliding range 12 closer and closer to the interconnecting part 53 in the course of time. This is exemplified by the consecutive FIGS. 4A, 4B and 4C which show consecutive stages, respectively, during growth of the spine 20. In FIGS. 4A, 4B and 4C, for purpose of elucidation only, deformation states of the U-shaped portion 50 are shown under the assumption that the torque T transmitted is equal throughout the three FIGS. 4A, 4B and 4C. Due to the nature of the U-shape, the torsional deformation of the U-shaped portion 50 is largest in FIG. 4A and smallest in FIG. 4C, as clearly seen in FIGS. 4A, 4B and 4C. This illustrates that the torsional stiffness of U-shaped portion 50, averagely speaking, becomes higher and higher in the course of time during growth of the spine 20.

Hence, from FIGS. 4A, 4B and 4C it is clear that in the mounted condition of FIG. 2's system 1, thanks to the U-shaped portion 50, under application of the corrective force action by the helical spring 3, in response to longitudinal growth of the spine 20, the responsive sliding of the second bone fixation element 32 relative to the elongated element 2 in the sliding range 12 away from the first location 11 causes said corrective force action to be higher than if in the sliding range the transverse cross-sectional shape of the elongated element 2 would have been the same as that of said single rod having a circular transverse cross-sectional circumference. Note, that in the shown example the U-shaped portion 50 has a transverse cross-sectional shape corresponding to two, mutually spaced circular transverse cross-sectional circumferences.

Evidently, the above explanation analogously applies to the U-shaped portion 60 and the helical spring 4 of system 1, since they are forming similar structure as U-shaped portion 50 and helical spring 3.

Figure 3:
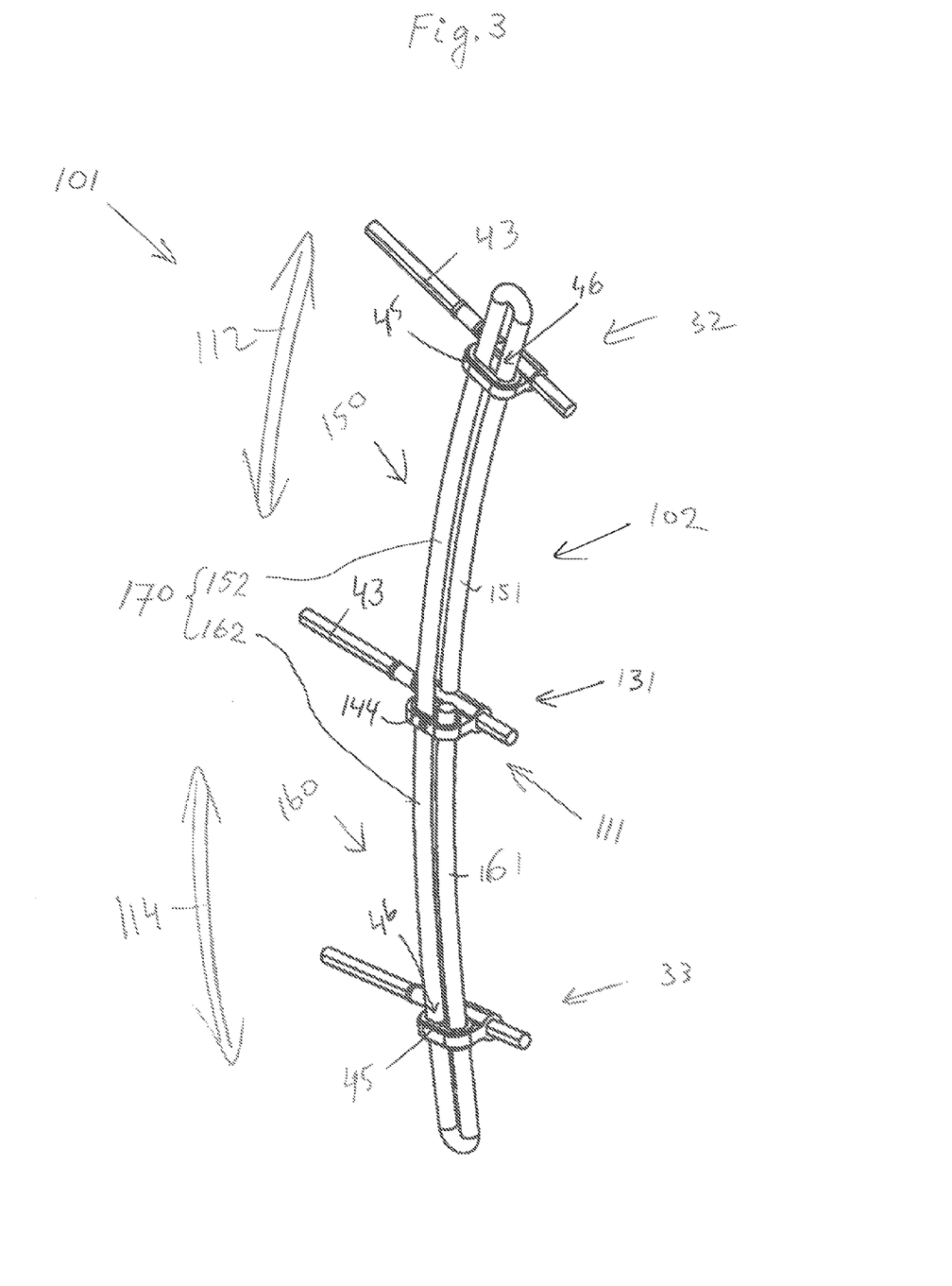
FIG. 3 shows, in a perspective view, an example of another embodiment of an implantation system according to the invention.

Reference is now made to FIG. 3, which shows the system 101 as an example of another embodiment of an implantation system according to the invention. System 101 comprises an elongated element 102, a first bone fixation element 131, a second bone fixation element 32 and another second bone fixation element 33. The elements 131, 32 and 33 of system 101, as well as their functions, are similar to the elements 31, 32 and 33, as well as their functions, respectively, of system 1 of FIG. 2. For simplicity, the bone fixators of the elements 131, 32 and 33 have not been shown in FIG. 3. The shown attachment element 144, by means of which the bridging part 43 of first bone fixation element 131 is fixedly attached to the elongated element 102, is similar to the attachment element 44 of FIG. 2.

Furthermore, the elongated element 102 of FIG. 3's system 101 comprises first and second U-shaped portions 150 and 160 similar to the first and second U-shaped portions 50 and 60, respectively, of FIG. 2's system 1, be it that the legs 151, 152 and 161, 162 of U-shaped portions 150 and 160 are relatively longer than the legs of U-shaped portions 50 and 60. The portions 150 and 160 are located relative to a first location 111, in a similar way as in FIG. 2 the portions 50 and 60 are located relative to the first location 11. In FIG. 3 the sliding ranges similar to the sliding ranges 12 and 14 have been indicated by reference numerals 112 and 114, respectively.

The major difference between the system 101 of FIG. 3 and the system 1 of FIG. 2 is, that the system 101 does not have helical springs, such as the helical springs 3 and 4 of system 1. Instead, the nonfree-ending leg 152 of U-shaped portion 150 is connected in-line with, in fact is integrally formed with, the nonfree-ending leg 162 of the other U-shaped portion 160, without any helical spring in-between. The integrally formed nonfree-ending legs 152 and 162 of U-shaped portions 150 and 160 together form a bending rod 170, which provides the element 102 at least with bending resilience. It is remarked that the bending rod 170 may also be designed so as to provide, by itself, the element 102 with additional torsional resilience in whatever degree.

A mounted condition of the implantation system 101 may for example be obtained when the first bone fixation element 131 is fixedly attached to vertebra 21 of FIG. 1, and the second bone fixation element 32 is fixedly attached to vertebra 22 of FIG. 1, and the other second bone fixation element 33 is fixedly attached to vertebra 23 of FIG. 1. The system 101 can be brought in its mounted condition in such manner that, by means of suitable pre-tensioning of the bending rod 170, this bending rod 170 in the mounted condition is resiliently applying, via the elements 131, 32 and 33 and via the vertebrae 21, 22 and 23, corrective bending force action to the spine 20 for correcting the defective lateral curvature of the spine 20.

Figure 5A:
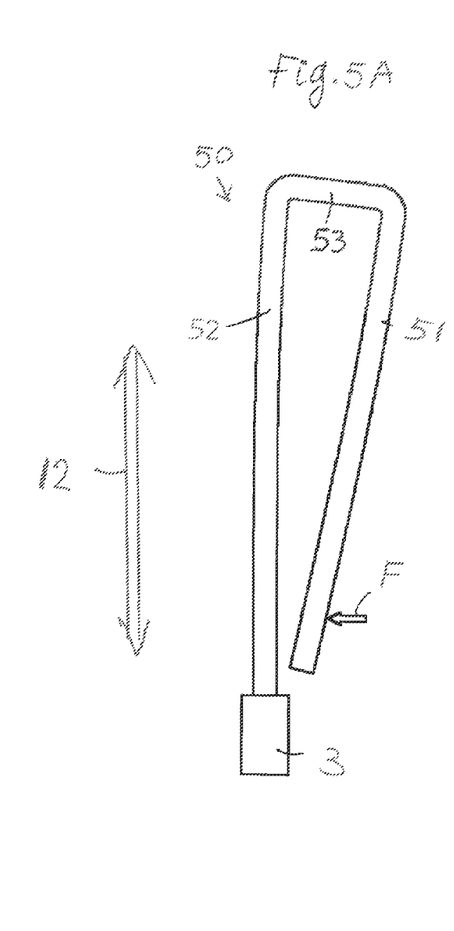
FIGS. 5A, 5B and 5C respectively show, in mutually identical plan views, another three different tensioned deformation states of the part shown in FIGS. 4A, 4B and 4C.
Figure 5B:
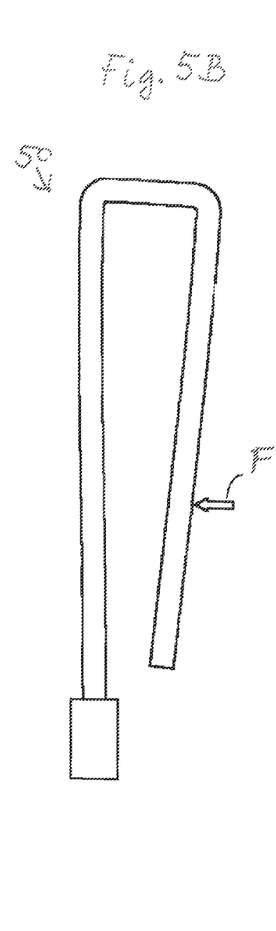
Figure 5C:
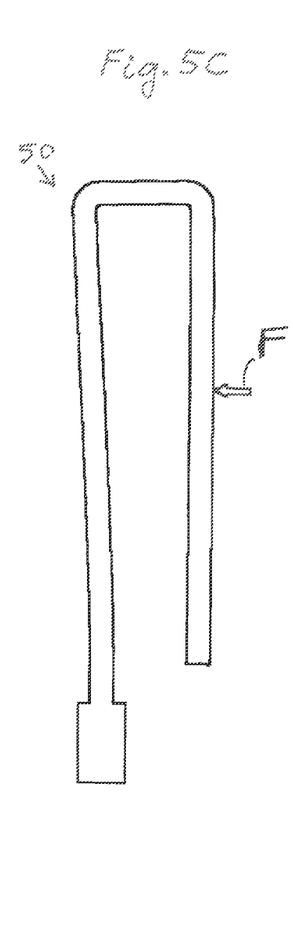
Figures 6A, 6B, 6C, 6D:
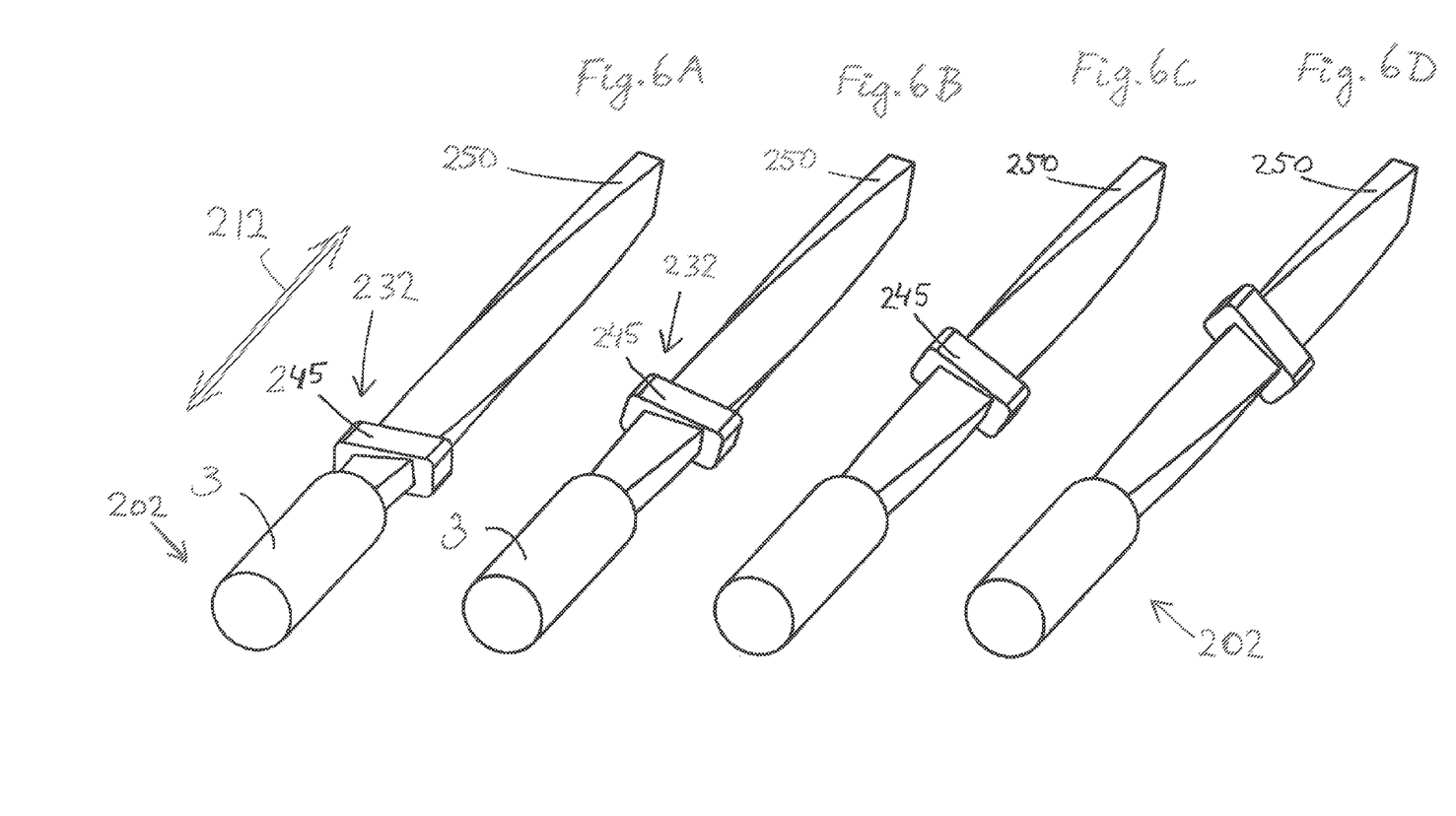
FIGS. 6A, 6B, 6C and 6D respectively show, in mutually identical perspective views, four differently slided states of an example of another embodiment of part of an elongated element of an implantation system according to the invention, said part extending at least in a sliding range as defined by the recited invention.

Now, with additional reference to FIGS. 5A, 5B and 5C, it is elucidated what happens when the spine 20 is growing in the course of time, which is the case when the system 101 of FIG. 3 is implanted into a growing child. It is noted that, although we are now elucidating the U-shaped portion 150 (or 160) of system 101, FIGS. 5A, 5B and 5C are showing the U-shaped portion 50 of system 1 again. This, however, does not make any difference for this elucidation, since the U-shaped portion 150 of system 101 is similar to the U-shaped portion 50 of system 1.

As already mentioned above, the sliding range 12 is extending along at least part of U-shaped portion 50. During longitudinal growth of the spine 20, vertebra 22 moves farther away from vertebra 21. This means that, averagely speaking, the connection element 45 will move farther away from the first location 11 in the course of time, i.e. in the direction of interconnecting part 53 of U-shaped portion 50. This means that the force being delivered by bending rod 170 and, via the U-shaped portion 50, being transmitted to the connection element 45, which force is indicated by the arrows F in FIGS. 5A, 5B and 5C, will, averagely speaking, be transmitted at locations in the sliding range 12 closer and closer to the interconnecting part 53 in the course of time. This is exemplified by the consecutive FIGS. 5A, 5B and 5C which show consecutive stages, respectively, during growth of the spine 20. In FIGS. 5A, 5B and 5C, for purpose of elucidation only, deformation states of the U-shaped portion 50 are shown under the assumption that the force F transmitted is equal throughout the three FIGS. 5A, 5B and 5C. Due to the nature of the U-shape, the lateral deformation of the U-shaped portion 50 is largest in FIG. 5A and smallest in FIG. 5C, as clearly seen in FIGS. 5A, 5B and 5C. This illustrates that the bending stiffness of U-shaped portion 50, averagely speaking, becomes higher and higher in the course of time during growth of the spine 20.

Hence, from FIGS. 5A, 5B and 5C it is clear that in the mounted condition of FIG. 3's system 101, thanks to the U-shaped portion 150, under application of the corrective force action by the bending rod 170, in response to longitudinal growth of the spine 20, the responsive sliding of the second bone fixation element 32 relative to the elongated element 102 in the sliding range 112 away from the first location 111 causes said corrective force action to be higher than if in the sliding range the transverse cross-sectional shape of the elongated element 2 would have been the same as that of said single rod having a circular transverse cross-sectional circumference. Note, that in the shown example the U-shaped portion 150 has a transverse cross-sectional shape corresponding to two, mutually spaced circular transverse cross-sectional circumferences.

Evidently, the above explanation analogously applies to the U-shaped portion 160 in relation to bending rod 170 of system 101, since it is forming similar structure as U-shaped portion 150 in relation to bending rod 170.

Reference is now made to FIGS. 6A, 6B, 6C and 6D, which show another embodiment of part of an elongated element 202 of an implantation system according to the invention. Said part may be used in FIG. 2's system 1 instead of U-shaped portion 50 in FIG. 2. Such an incorporation of said part in system 1 is considered here, which is the reason why, similar to FIGS. 4A, 4B and 4C, FIGS. 6A, 6B, 6C and 6D show part of the helical spring 3. Hence, instead of U-shaped portion 50, the elongated element, now identified with reference numeral 202, comprises a helically shaped element 250, hereinafter referred to as helical strip 250. Furthermore, instead of FIG. 2's connection element 45, the elongated element 202 co-operates with another connection element 245 of the concerning second bone fixation element 232, which connection element 245 is arranged for contactingly sliding along helical strip 250 in the indicated sliding range 212.

The helical strip 250 and connection element 245 function as helically shaped guiding structure defining a helical path for guiding the second bone fixation element 232 relative to the elongated element 202 in the sliding range 212. When the second bone fixation element 232 slides along the helical strip 250 in longitudinal direction of the elongated element 202, the orientation of the second bone fixation element 232 relative to the helical strip 250 follows said helical path.

It is now assumed that the system 1, at the time of its implantation relative to the spine 20, has been brought in its mounted condition in such manner that, by means of suitable pre-tensioning of the helical spring 3, this helical spring 3 in the mounted condition is resiliently applying, via the elements 31 and 232 and via the vertebrae 21 and 22, corrective torsional force action to the spine 20 for correcting the defective torsional curvature of the spine 20.

Now, with reference to FIGS. 6A, 6B, 6C and 6D, it is elucidated what happens when the spine 20 is growing in the course of time, which is the case when the system 1 is implanted into a growing child. During longitudinal growth of the spine 20, vertebra 22 moves farther away from vertebra 21. This means that, averagely speaking, the connection element 245 will move farther away from the first location 11 in the course of time, i.e. in the direction away from the helical spring 3. FIGS. 6A, 6B, 6C and 6D show consecutive stages, respectively, during such growth of the spine 20. As explained, the orientation of the second bone fixation element 232 relative to the helical strip 250 follows a helical path then.

Hence, from FIGS. 6A, 6B, 6C and 6D it is clear that, when a suitable direction of the helical pitch of the first helical strip 250 has been chosen in dependence of the direction in which the helical spring 3 is pre-tensioned, under application of the corrective force action by the helical spring 3, in response to longitudinal growth of the spine 20, the responsive sliding of the second bone fixation element 232 relative to the elongated element 202 in the sliding range 212 away from the helical spring 3 causes said corrective force action to be higher than if in the sliding range the transverse cross-sectional shape of the elongated element 202 would have been the same as that of said single rod having a circular transverse cross-sectional circumference.

In the foregoing specification, the invention has been described with reference to specific examples of embodiments of the invention. However, various modifications and changes may be made therein without departing from the broader scope of the invention as set forth in the appended claims.

For example, in the shown embodiments, a system according to the invention comprises only one first bone fixation element and two second bone fixation elements for an elongated element. Various alternative configurations are possible. For example, it is possible to apply for an elongated element only one second bone fixation element, instead of two. Also it is possible to apply for an elongated element two, three, four, or more first bone fixation elements and three, four, or more second bone fixation elements, as well as any possible combinations of such numbers of first and second bone fixation elements for an elongated element.

Furthermore, an implantation system according to the invention may comprise a plurality of elongated elements, each one of said plurality being associated with the same at least one first bone fixation element and with the same at least one second bone fixation element. An example of such a system is e.g. obtained when the elongated element 102 of FIG. 3 by means of the attachment element 144 and the two connection elements 45 of FIG. 3 is connected to the three bridging parts 43 shown in FIG. 2 in such manner that the elongated elements 2 and 102 are extending side by side relative to one another.

Also, it is possible to integrate within a single one of the at least one elongated element of a system according to the invention, the functions of both a bending rod and a torsional spring, thus efficiently and compactly deriving benefit regarding maintaining suitable levels of both corrective bending force action and corrective torsional force action during growth of a spine, by means of only a single U-shaped portion. This way, benefit is derived from the combined effects described with reference to FIGS. 4A, 4B and 4C, on the one hand, and with reference to FIGS. 5A, 5B and 5C, on the other hand.

Furthermore, it is also possible to apply a U-shaped portion, whose legs are nonparallel relative to one another. For example, the legs of a U-shaped portion may extend in helical shapes, more or less analogous to the helical shape of the helical strip shown in FIGS. 6A, 6B, 6C and 6D. This way benefit is derived from the combined effects described with reference to FIGS. 4A, 4B and 4C and/or FIGS. 5A, 5B and 5C, on the one hand, and with reference to FIGS. 6A, 6B, 6C and 6D, on the other hand.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

The invention claimed is:

1. An implantation system configured to treat a defective curvature of the spinal column of a patient; the system comprising:
at least one element being elongated in a longitudinal direction;
at least one first bone fixation element configured to be fixedly attached to a first vertebra of said spinal column, the first bone fixation element being fixedly attached to said elongated element at a first location along said longitudinal direction of the elongated element;
at least one second bone fixation element configured to be fixedly attached to a second vertebra of said spinal column, said second vertebra being different from said first vertebra; and
a guiding structure through which the second bone fixation element is slidably and contactingly connected to the elongated element for guiding the second bone fixation element relative to the elongated element in a sliding range along said longitudinal direction; said sliding range being distant from said first location;
wherein the elongated element has bending resilience and/or torsional resilience for resiliently applying in a mounted condition of the implantation system via said first and second bone fixation elements and via said first and second vertebrae, corrective bending and/or torsional force action to said spinal column for correcting said defective curvature;
wherein said guiding structure is realized in that the elongated element is shaped to comprise a resilient U-shaped portion, said U-shaped portion having two legs and an interconnecting part interconnecting said two legs, wherein said U-shaped portion with its interconnecting part is facing away from said first location; wherein one of said two legs is a free ending leg of the elongated element, said free ending leg having a bending resilience, wherein said sliding range is extending along at least part of said U-shaped portion, and wherein said sliding and contacting connection is present between the second bone fixation element and at least said free ending leg of the U-shaped portion in that said guiding structure comprises a passageway which has a slot-like transverse cross-sectional shape which allows said two legs of the U-shaped portion, both of which are extending through said passageway, to laterally move towards and away from one another when one or both of said two legs are resiliently deforming.

2. The implantation system according to claim 1, characterized in that in at least part of said sliding range the transverse cross-sectional shape of said elongated element is different from that of a single rod having a circular transverse cross-sectional circumference; and
in that said guiding structure is configured such that, in said mounted condition and under application of said corrective force action, in response to longitudinal growth of said spinal column the responsive sliding of said second bone fixation element relative to said elongated element in said at least part of said sliding range away from the first location causes said corrective force action to be higher than if in said at least part of said sliding range the transverse cross-sectional shape of the elongated element would have been the same as that of said single rod having a circular transverse cross-sectional circumference.

3. The implantation system according to claim 1, wherein said guiding structure comprises a helically shaped structure defining a predetermined helical path for said guiding the second bone fixation element relative to the elongated element in the sliding range.

4. The implantation system according to claim 3, wherein said helically shaped structure is realized in that the elongated element is shaped to comprise a helically shaped portion wherein said sliding range is extending along at least part of said helically shaped portion, and wherein said sliding and contacting connection is present between the second bone fixation element and said helically shaped portion in such manner that, when the second bone fixation element helically slides along said helically shaped portion in said longitudinal direction, the orientation of the second bone fixation element relative to said helically shaped element follows said predetermined helical path.

5. The implantation system according to claim 1, comprising at least two specimens of said at least one second bone fixation element, each of said two specimens being associated with the same elongated element, wherein said two specimens are mutually lying on opposite sides of said first location; one of said two specimens being associated with a first corresponding one of said second vertebra and with a first corresponding one of said sliding range, the other one of said two specimens being associated with a second corresponding one of said second vertebra and with a second corresponding one of said sliding range.

6. The implantation system according to claim 1, comprising a plurality of said at least one elongated element, each one of said plurality being associated with the same first bone fixation element and with the same second bone fixation element.

7. The implantation system according to claim 1, wherein at least one of said first bone fixation element comprises two first bone fixators, being mutually spaced in a direction transverse to said longitudinal direction, and a first bridging part, which fixedly attaches the two first bone fixators relative to one another, and which bridging part is fixedly attached to the elongated element at said first location, each of said two first bone fixators fixedly attached to one and the same vertebra.

8. The implantation system according to claim 1, wherein at least one of said second bone fixation element comprises two second bone fixators, being mutually spaced in a direction transverse to said longitudinal direction, and a second bridging part, which fixedly attaches the two second bone fixators relative to one another, and wherein said sliding and contacting connection is present between said second bridging part and the elongated element, each of said two second bone fixators configured to be fixedly attached to one and the same vertebra.

9. An implantation system configured to treat a defective curvature of the spinal column of a patient, the system comprising:
at least one element being elongated in a longitudinal direction;
at least one first bone fixation element configured to be fixedly attached to a first vertebra of said spinal column, the first bone fixation element being fixedly attached to said elongated element at a first location along said longitudinal direction of the elongated element;
at least one second bone fixation element configured to be fixedly attached to a second vertebra of said spinal column, said second vertebra being different from said first vertebra; and
a guiding structure through which the second bone fixation element is slidably and contactingly connected to the elongated element for guiding the second bone fixation element relative to the elongated element in a sliding range along said longitudinal direction, said sliding range being distant from said first location;
wherein the elongated element has bending resilience and/or torsional resilience for resiliently applying in a mounted condition of the implantation system via said first and second bone fixation elements and via said first and second vertebrae, corrective bending and/or torsional force action to said spinal column for correcting said defective curvature; and wherein said guiding structure comprises a helically shaped structure defining a predetermined helical path for said guiding the second bone fixation element relative to the elongated element in the sliding range; and
wherein said helically shaped structure is realized in that the elongated element is shaped to comprise a helically shaped portion wherein said sliding range is extending along at least part of said helically shaped portion, and wherein said sliding and contacting connection is present between the second bone fixation element and said helically shaped portion in such manner that, when the second bone fixation element helically slides along said helically shaped portion in said longitudinal direction, the orientation of the second bone fixation element relative to said helically shaped element follows said predetermined helical path.

10. The implantation system according to claim 9, characterized in that in at least part of said sliding range the transverse cross-sectional shape of said elongated element is different from that of a single rod having a circular transverse cross-sectional circumference; and in that said guiding structure is configured such that, in said mounted condition and under application of said corrective force action, in response to longitudinal growth of said spinal column the responsive sliding of said second bone fixation element relative to said elongated element in said at least part of said sliding range away from the first location causes said corrective force action to be higher than if in said at least part of said sliding range the transverse cross-sectional shape of the elongated element would have been the same as that of said single rod having a circular transverse cross-sectional circumference.

11. The implantation system according to claim 9, wherein said guiding structure is realized in that the elongated element is shaped to comprise a resilient U-shaped portion, said U-shaped portion having two legs and an interconnecting part interconnecting said two legs, wherein said U-shaped portion with its interconnecting part is facing away from said first location, wherein one of said two legs is a free ending leg of the elongated element, said free ending leg having bending resilience, wherein said sliding range is extending along at least part of said U-shaped portion, and wherein said sliding and contacting connection is present between the second bone fixation element and at least said free ending leg of the U-shaped portion in that said guiding structure comprises a passageway which has a slot-like transverse cross-sectional shape which allows said two legs of the U-shaped portion, both of which are extending through said passageway, to laterally move towards and away from one another when one or both of said two legs are resiliently deforming.

12. The implantation system according to claim 9, comprising at least two specimens of said at least one second bone fixation element, each of said two specimens being associated with the same elongated element, wherein said two specimens are mutually lying on opposite sides of said first location, one of said two specimens being associated with a first corresponding one of said second vertebra and with a first corresponding one of said sliding range, the other one of said two specimens being associated with a second corresponding one of said second vertebra and with a second corresponding one of said sliding range.

13. The implantation system according to claim 9, comprising a plurality of said at least one elongated element, each one of said plurality being associated with the same first bone fixation element and with the same second bone fixation element.

14. The implantation system according to claim 9, wherein at least one of said first bone fixation element comprises two first bone fixators, being mutually spaced in a direction transverse to said longitudinal direction, and a first bridging part, which fixedly attaches the two first bone fixators relative to one another, and which bridging part is fixedly attached to the elongated element at said first location, each of said two first bone fixators fixedly attached to one and the same vertebra.

15. The implantation system according to claim 9, wherein at least one of said second bone fixation element comprises two second bone fixators, being mutually spaced in a direction transverse to said longitudinal direction, and a second bridging part, which fixedly attaches the two second bone fixators relative to one another, and wherein said sliding and contacting connection is present between said second bridging part and the elongated element, each of said two second bone fixators configured to be fixedly attached to one and the same vertebra.

* * * * *